(12) United States Patent
Egami et al.

(10) Patent No.: US 9,626,486 B2
(45) Date of Patent: Apr. 18, 2017

(54) PATIENT HEALTH CARE NETWORK GUIDED ENCOUNTER

(75) Inventors: Tadashi Egami, Belmont, CA (US); Gilbert C. Lemke, Los Gatos, CA (US); John C. Ryan, Boston, MA (US)

(73) Assignee: Koninklijke Philips N.V., Eindhoven (NL)

( * ) Notice: Subject to any disclaimer, the term of this patent is extended or adjusted under 35 U.S.C. 154(b) by 426 days.

(21) Appl. No.: 12/446,983

(22) PCT Filed: Oct. 31, 2007

(86) PCT No.: PCT/US2007/083077
§ 371 (c)(1),
(2), (4) Date: Apr. 24, 2009

(87) PCT Pub. No.: WO2008/060853
PCT Pub. Date: May 22, 2008

(65) Prior Publication Data
US 2010/0094646 A1 Apr. 15, 2010

Related U.S. Application Data

(60) Provisional application No. 60/865,036, filed on Nov. 9, 2006.

(51) Int. Cl.
*G06Q 10/00* (2012.01)
*G06Q 50/00* (2012.01)
(Continued)

(52) U.S. Cl.
CPC ...... *G06F 19/3481* (2013.01); *G06F 19/3418* (2013.01); *G06Q 50/22* (2013.01); *G06F 19/3456* (2013.01); *G06F 19/3475* (2013.01)

(58) Field of Classification Search
USPC ........................................ 705/2–3
See application file for complete search history.

(56) References Cited

U.S. PATENT DOCUMENTS 5,879,163 A 3/1999 Brown et al.
5,887,133 A 3/1999 Brown et al.
(Continued)

FOREIGN PATENT DOCUMENTS

JP 2002117153 A 4/2002
JP 2004240553 A 8/2004
(Continued)

OTHER PUBLICATIONS

Macbeth, Microsoft Developer: The Daily Task List: Tasks on the Calendar, Jan. 5, 2006 https://blogs.msdn.microsoft.com/melissamacbeth/2006/01/05/the-daily-task-list-tasks-on-the-calendar/.*
(Continued)

*Primary Examiner* — Amber A Misiaszek

(57) ABSTRACT

In an environment where it is beneficial for chronic health care patients to receive individualized attention on a daily basis, a health care network (10) is provided. Each patient receives a user interface device (12) such as a set top box for accessing the network (10). Based on the patient's health care history, a nurse or other health care professional interfaces with a server (22) and constructs a care plan specific to that patient by filling out appropriate sections of a care plan template. An itinerary arrangement processor (32) organizes content gleaned from the patient's care plan and constructs a serially arranged itinerary for the patient to experience each day. The patient logs on to the network (10) and is immediately presented with the day's itinerary, without having to navigate any menus. Resultantly, the patient will have an easier experience, and will not miss any material.

23 Claims, 8 Drawing Sheets

Figure 1:
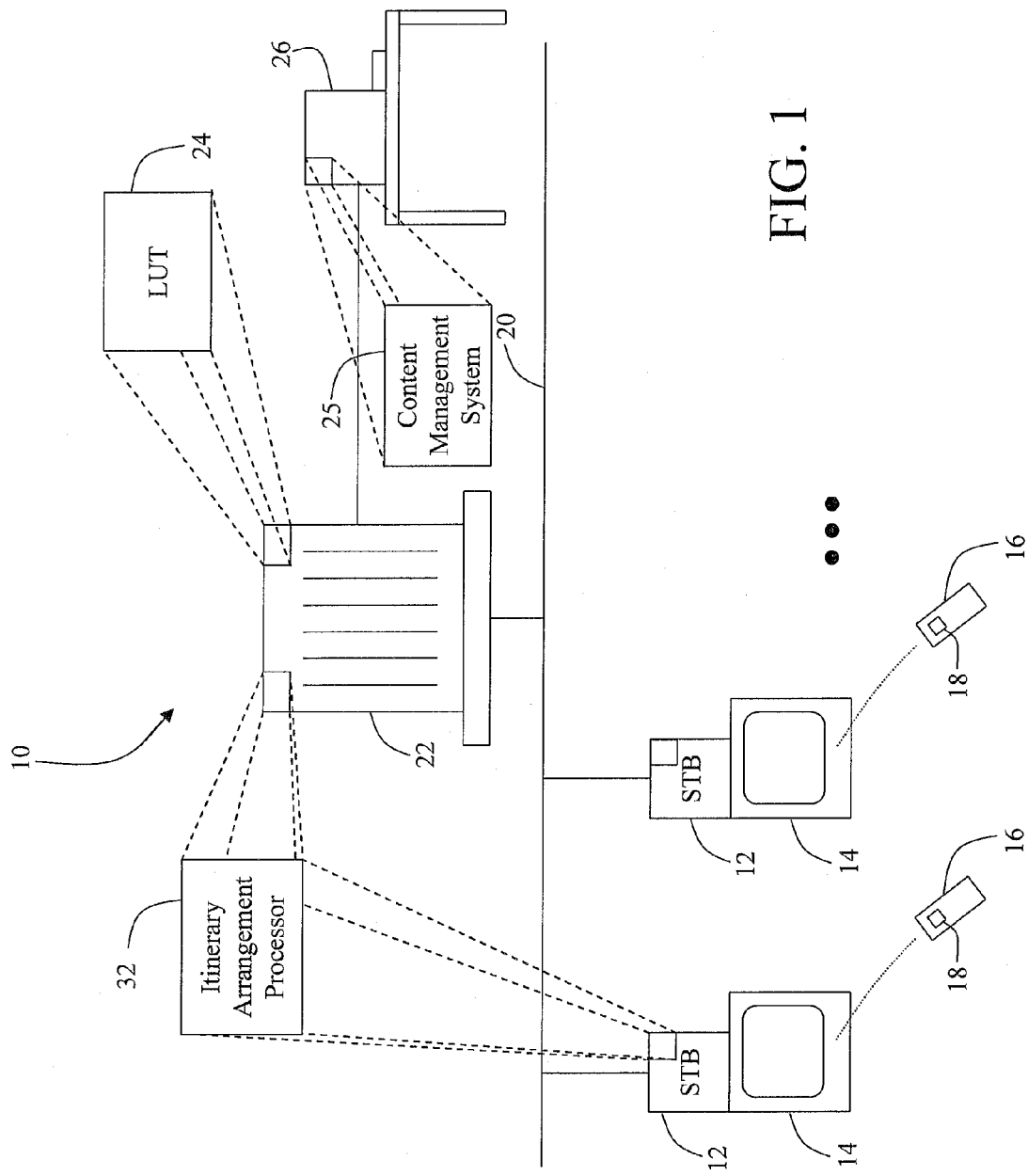

(51) Int. Cl.
*G06F 19/00* (2011.01)
*G06Q 50/22* (2012.01)

(56) References Cited

U.S. PATENT DOCUMENTS

| | | | |
|---|---|---|---|
| 5,897,493 A | 4/1999 | Brown | |
| 5,960,403 A | 9/1999 | Brown | |
| 5,997,476 A | 12/1999 | Brown | |
| 6,101,478 A | 8/2000 | Brown | |
| 6,168,563 B1 | 1/2001 | Brown | |
| 6,248,065 B1 | 6/2001 | Brown | |
| 6,290,646 B1 | 9/2001 | Cosentino et al. | |
| 6,375,469 B1 | 4/2002 | Brown | |
| 6,401,085 B1* | 6/2002 | Gershman et al. | |
| 6,454,705 B1 | 9/2002 | Cosentino et al. | |
| 6,723,045 B2 | 4/2004 | Cosentino et al. | |
| 6,755,783 B2 | 6/2004 | Cosentino et al. | |
| 6,968,375 B1 | 11/2005 | Brown | |
| 7,185,282 B1* | 2/2007 | Naidoo | A61B 5/0002 348/E7.071 |
| 2001/0012913 A1* | 8/2001 | Iliff | G06F 19/322 600/300 |
| 2002/0133377 A1 | 9/2002 | Brown | |
| 2003/0069753 A1 | 4/2003 | Brown | |
| 2003/0163351 A1 | 8/2003 | Brown et al. | |
| 2003/0229513 A1* | 12/2003 | Spertus | G06Q 10/10 705/2 |
| 2004/0019259 A1 | 1/2004 | Brown et al. | |
| 2004/0102685 A1 | 5/2004 | Cosentino et al. | |
| 2004/0117207 A1 | 6/2004 | Brown | |
| 2004/0117208 A1 | 6/2004 | Brown | |
| 2004/0117209 A1 | 6/2004 | Brown | |
| 2004/0219500 A1 | 11/2004 | Brown et al. | |
| 2004/0249672 A1 | 12/2004 | Bocionek et al. | |
| 2005/0027562 A1 | 2/2005 | Brown | |
| 2005/0080652 A1 | 4/2005 | Brown | |
| 2005/0086083 A1 | 4/2005 | Brown | |
| 2005/0172021 A1 | 8/2005 | Brown | |
| 2005/0172022 A1 | 8/2005 | Brown | |
| 2005/0228883 A1 | 10/2005 | Brown | |
| 2005/0235060 A1 | 10/2005 | Brown | |
| 2005/0273509 A1 | 12/2005 | Brown | |
| 2006/0004611 A1 | 1/2006 | Brown | |
| 2006/0015017 A1 | 1/2006 | Cosentino et al. | |
| 2006/0080152 A1 | 4/2006 | Brown | |
| 2006/0089969 A1 | 4/2006 | Brown et al. | |
| 2006/0100910 A1 | 5/2006 | Brown | |
| 2006/0111941 A1* | 5/2006 | Blom | 705/2 |
| 2006/0167735 A1* | 7/2006 | Ward | G06Q 10/06311 705/2 |
| 2007/0198432 A1* | 8/2007 | Pitroda et al. | 705/64 |

FOREIGN PATENT DOCUMENTS

| | | |
|---|---|---|
| JP | 2005080270 A | 3/2005 |
| JP | 2005333288 A | 12/2005 |
| JP | 2006520030 A | 8/2006 |
| WO | 9712544 A1 | 4/1997 |
| WO | 0225551 A1 | 3/2002 |
| WO | 2005006969 A1 | 1/2005 |

OTHER PUBLICATIONS

Guillen, S., et al.; Multimedia Telehomecare System Using Standard TV set; 2002; IEEE Trans. on Biomedical Engineering; 49(12)1431-1437.

Prentza, A., et al.; Intranet Health Clinic-A web-based interactive communication environment for the continuation in health care; 1999; Future Generation Computer Systems; 15:277-285.

* cited by examiner

Welcome to the
Motiva
Personal
Healthcare
Channel

Please enter your
code number

Good morning
Bruce Thomas

FIG. 5

Today's Activities:

- Watch video
- Take Survey or Quiz
- Main menu
- Press any key to begin

FIG. 6

Today's Video:

Hypoglycemia

Run time: 6 minutes
Point value: 1 point
This video covers the
Causes, prevention, and
treatment of Hypoglycemia
(low blood glucose).

FIG. 7

Playing Video

Hypoglycemia

FIG. 8

Save Video?

Would you like to save this video so that
You can view it again another day?

☑ Yes, save it

☐ No, don't save it

FIG. 9

Today's Activities:

☑ Watch video
- Take Survey or Quiz
- Main menu
- Press any key
  to begin

FIG. 10

Quiz on Hypoglycemia

When Bill took his blood glucose reading, it was 68 mg/dl.
What should Bill do?

☐ Fast for 15 minutes

☑ Drink a glass of fruit juice

☐ Exercise

☐ Take a nap

FIG. 11

Congratulations!

You've finished your current goal: Understanding Diabetes.
Press any key for More options

FIG. 12

PATIENT HEALTH CARE NETWORK GUIDED ENCOUNTER

CROSS REFERENCE TO RELATED APPLICATIONS

This application claims the benefit of U.S. provisional application Ser. No. 60/865,036 filed Nov. 9, 2006 which is incorporated herein by reference.

The present application relates to ongoing health care for patients with chronic illnesses or long term medical conditions. More specifically, the present application is directed to a secure, personalized platform service that connects patients that may not be technologically savvy and their care team. This enables healthcare organizations to effectively and efficiently empower and assist their patients in managing their health and lifestyle despite the sometimes daunting prospect of dealing with modern technology.

Patients who have healthcare issues often have lifestyle issues which complicate the medical issues. For example, diabetes can be aggravated by diet, lack of exercise, obesity, and the like. One system for helping these patients to manage their disease, adjust their lifestyle, and the like, provides each patient with personalized programming. The patient is provided with a care plan that manifests itself in a series of educational or motivational programs directed to their specific healthcare issues. For example, the patient might be provided with educational and motivational programming at the same time each day to assist the patient in establishing and maintaining a diet and exercise regimen. The programming is provided on disc, from a programming memory, or from a central source, such as the hospital or medical care facility that has prescribed the programming and travels over a public communications network to the patient's home. There, a set top box decodes the signals intended for the specific patient and displays them on the patient's television, and the patient can interact with the programming using their TV or set top box remote. The set top box provides for user feedback, such as weigh-ins, blood pressure readings, and the like, to be communicated from the patient to the healthcare facility.

Although such systems are successful, one drawback is that this type of care plan distribution is often intended for elderly patients, who are not always well versed in navigating electronic media. Memory loss is also often an additional roadblock in providing care to elderly patients. Technologically complex systems can confuse and frustrate such patients. There is a danger that patients of this kind will miss vital portions of their individualized care plan not because of apathy or stubbornness, but due to difficulties of navigating technology that with which they are not familiar.

The present application provides a new and improved apparatus and method of content presentation which overcomes the above-referenced problems and others.

In accordance with one aspect, a medical health care network is provided. At least one server contacts at least one user interface device periodically. The server houses a care plan that includes a series of content elements to be presented over time for a patient. An itinerary arrangement processor extracts information regarding the patient's health care from the care plan and selects content elements to be displayed for the patient in a daily viewing session and arranges the content elements into a serially ordered itinerary for presentation to the patient. This order is defined by a care plan designer at the time of care plan creation. The care plan designer will be given the flexibility to order the content by type (e.g., all messages first, then all videos, etc.) or by topic (e.g., a "Nutrition" message, video, and survey first, followed by an "Exercise" message, video, and quiz set).

A display device displays the content elements to the patient. An interface device causes the display to display the content elements selected by the itinerary arrangement processor. A user input device enables a patient to commence a first and each subsequent content element.

In accordance with another aspect, a method of presenting health care information to a patient is provided. A care plan is generated that includes a series of content elements to be presented over time for the patient. A viewing session's worth of content elements are extracted from the care plan to be displayed to the patient. The viewing session's content may be introduced by a video character, which greets the patient in both audio and video and tells the patient exactly what content elements the patient will experience that day. The narration character may also reappear periodically throughout the viewing session's structured encounter. After the initial greeting, the viewing session's content elements are arranged into a serially ordered itinerary. After the patient logs on to a secure health care information network, the itinerary is presented to the patient. The patient is then prompted to commence the viewing session's itinerary, possibly by a friendly video character guide. After the patient selects a commencement action, a first of the content elements is displayed to the patient. After the first content element is complete, the patient is prompted to continue with the next content element. The steps of displaying and prompting the patient to continue with subsequent content elements are repeated until all content elements have been displayed to the patient and completed by the patient as required.

In accordance with another aspect, a content server that connects to a public network is presented. The server includes a look up table or memory that contains care plan content elements for a plurality of care plans for a plurality of patients. The server also includes an itinerary arrangement processor that queries the look up table or memory to select a series of content elements to be presented to each patient in a next daily session in a preselected order such that the order that the patient is shown a serial presentation of content elements is not alterable by the patient.

One advantage is that a guided encounter is easier to use. For some patients, this determines the effectiveness of their care experience. For still other patients, it will make the difference between being able or not being able to use the system.

Another advantage resides in patients missing less content e.g., the information they need to care for themselves, or the information they need to provide in order to enable the clinical team to properly care for them.

Another advantage is the care experience can be tailored along two dimensions: the amount of flexibility in choosing a path through the application, and the amount of interaction required of the patient.

Another advantage resides in an increased amount of flexibility. The experience can be tailored to the mental acuity of the patient, such that patients with greater cognitive skills and experience with computers can be given more flexibility in determining their own path through the application for their daily experience, while patients with lower cognitive skills will be given less flexibility by the care team to select their path through their daily experience.

Another advantage resides in the flexibility of the amount of required interaction. The care giver may determine the level of feedback from the patients. For instance, the care giver may determine that complaint patients do not need to "drive" the interaction forward by pushing buttons. Alternatively, the nurse may determine that the patient would benefit more from contributing to the experience, and may require other certain patients to move the experience forward by selecting options on the input device.

Another advantage is that it makes working with technology less daunting.

Another advantage is that the patient will feel "successful" in caring for themselves, that this is something that they can do, which will encourage them to be more compliant with their care plan.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 2:
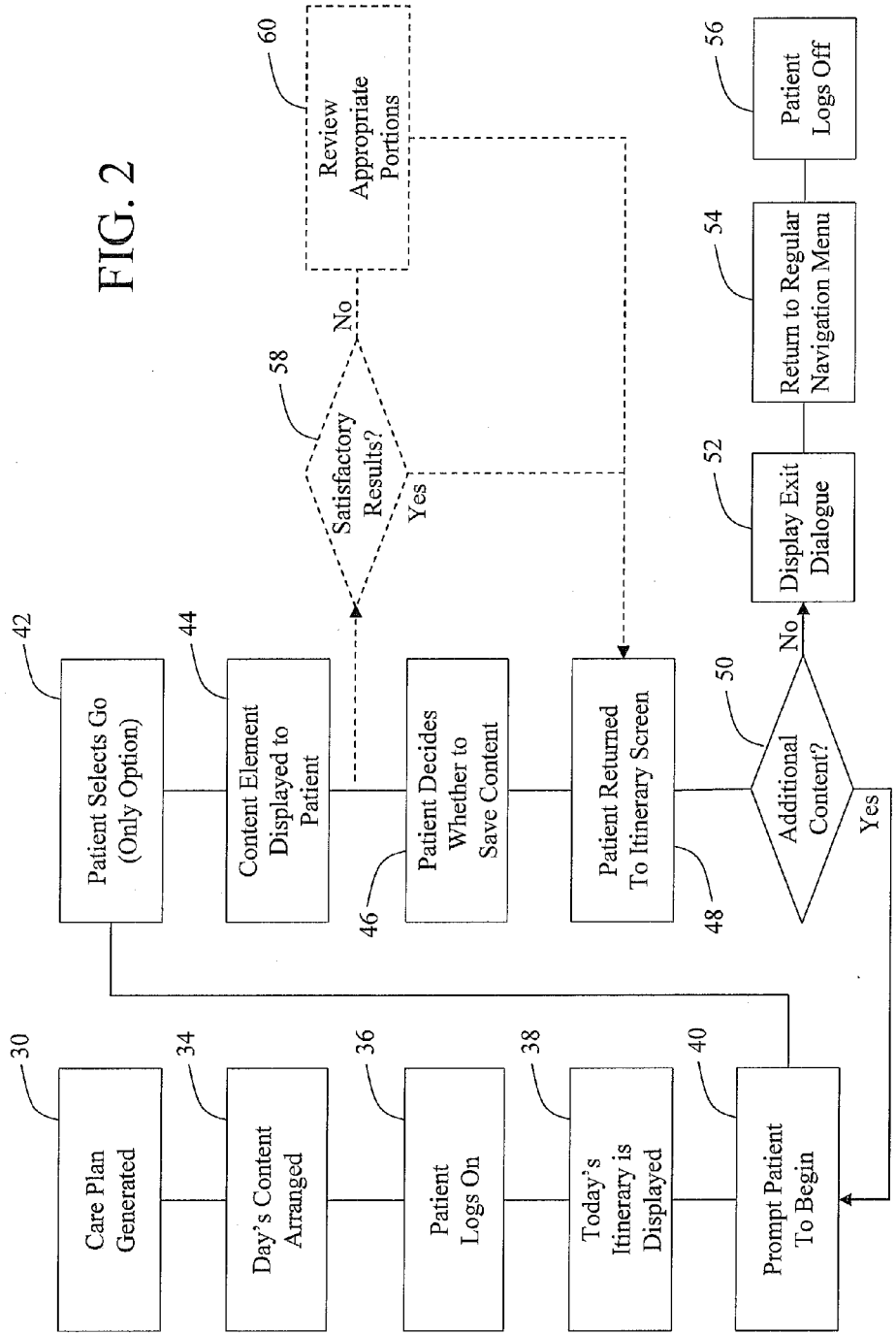
Figures 3, 4:
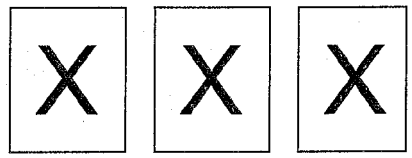
Figure 13:
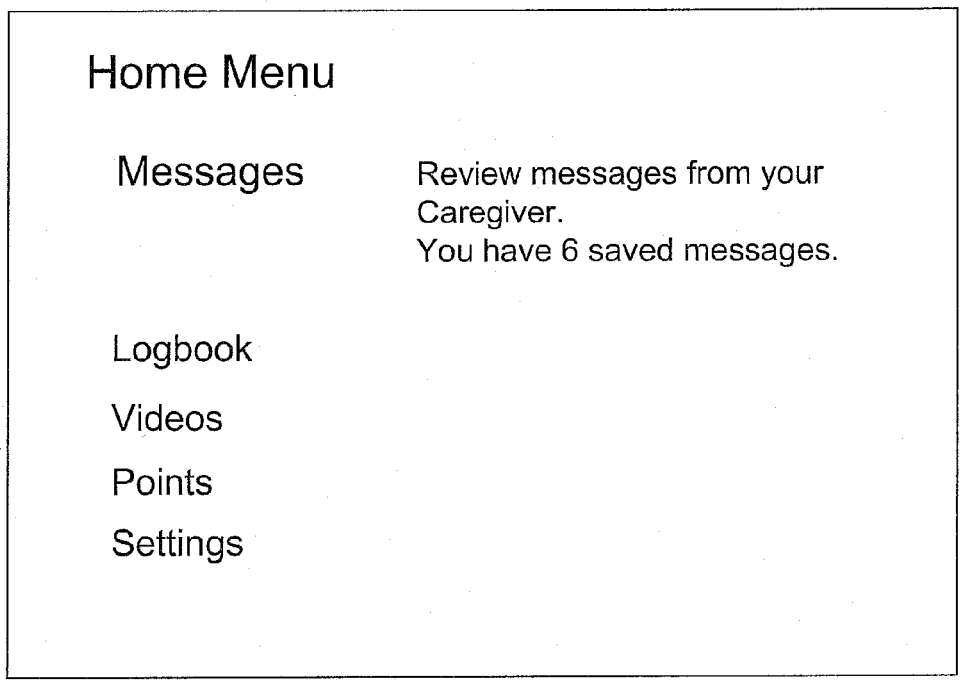
Figure 14:
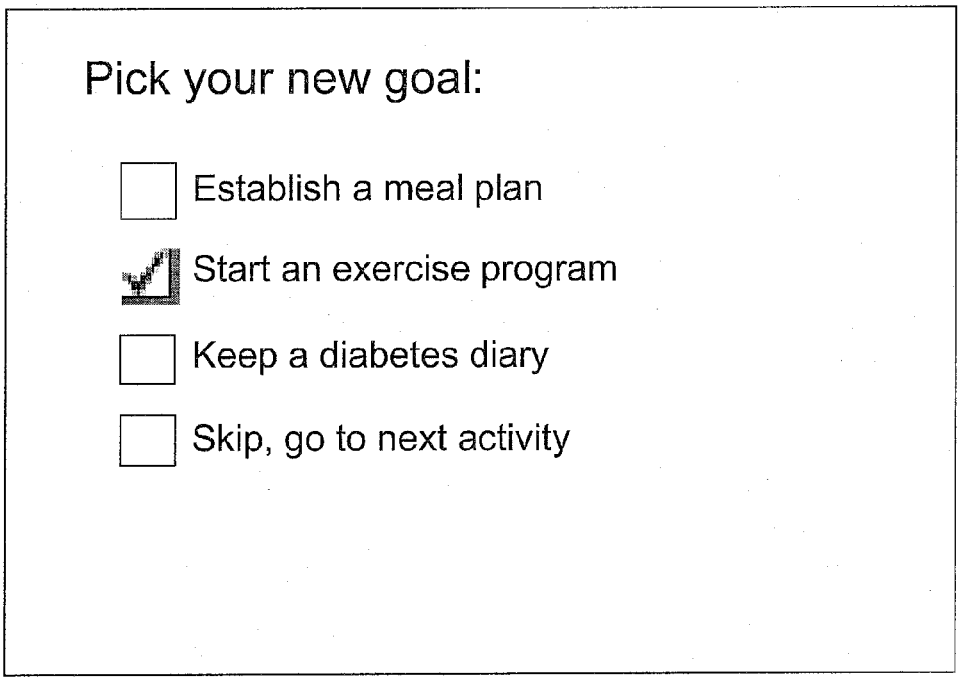

FIG. 1 is an illustration of a patient healthcare network;
FIG. 2 is a flowchart outlining a typical guided encounter;
FIG. 3 is an exemplary startup screen;
FIG. 4 is an exemplary login screen;
FIG. 5 is an exemplary welcome screen;
FIG. 6 is an exemplary itinerary screen;
FIG. 7 is an exemplary content overview screen;
FIG. 8 is an exemplary content viewing screen;
FIG. 9 is an exemplary content save option screen;
FIG. 10 is an exemplary itinerary screen with a partially complete itinerary;
FIG. 11 is an exemplary survey question screen;
FIG. 12 is an exemplary congratulatory screen;
FIG. 13 is an exemplary navigational menu screen;
FIG. 14 is an exemplary user feedback screen.

With reference to FIG. 1, a medical care network 10 is illustrated. When physicians prescribe short term care such as a finite amount of prescription drugs, rest, and the like, once the patient takes all the pills, etc., the treatment is complete. In many situations, however, the patient is diagnosed with a long term illness or chronic condition that can require long term care and/or lifestyle changes. In this type of situation, the healthcare professional may prescribe habits or behaviors that were not previously a part of the patient's daily regimen. The patient, motivated by his or her visit with the doctor, may start out with this new treatment with the best intentions, but as time lapses, it is easy to slip back into old habits. For instance, a patient may go to his doctor and be diagnosed with diabetes. The doctor recommends that the patient eat better, exercise more, and check his insulin levels regularly. Motivated by the newly perceived risk to his health, the patient goes on a diet and exercises. As time goes on, however, the patient starts to lapse back into his old behaviors, and eventually forgets diet and exercise, and possibly regular insulin checks. The healthcare network 10 is designed to help keep chronic care patients motivated by providing a dynamic care giving experience even long after any given visit to a doctor and to provide health related feedback from the patient to the caregiver.

The healthcare network 10 includes a plurality of individual user interface devices 12, such as a set top box, processor, or other such interface device, which is associated with a display 14, such as a user's television set, monitor, or other display device. The patient logs onto the network 10 by using the interface device 12. The interface 12 may be a separate set top box, or may be integrated into the display 14 itself. The interface device 12 also interacts with an input device 16, such as a handheld remote, touchscreen, keyboard, mouse, or other similar device, through which the patient can enter information, such as passwords, responses to questionnaires, health related readings such as weight or blood pressure, and the like. The input device 16 includes at least one key 18, but in another embodiment includes a plurality of keys. The input device 16 is preferred to have large keys with distinct markings such as color, shape, and/or labeling that clearly delineate the intended use or functionality.

The interface devices 12 connect or interface with a public network 20, such as an interactive cable TV network, the internet, or the like. Although acting over a public or private network 20, the user interface device 12 communicates over a secure layer of that network 20 to protect sensitive information of the patient. Through the public network 20, the interface device 12 communicates with various servers such as a local server 22. The server 22 includes a look-up-table or database 24 of patient care plans. This database 24 houses the care plans that have been synthesized for all the patients in the network 10 for which this particular server 22 is responsible. A care plan is preferably synthesized by a nurse manager or other health care professional based on the patient's medical history. To create a care plan, the health care professional reviews the patient's medical history, and inputs information to a generic care plan template. The system also includes a content management system 25 for uploading, versioning, and previewing content for the health care professional. The content management system 25 also includes a facility to experience what the patient would actually see before actually deploying the media content to the patients.

The health care professional inputs the information to the template via a user interface 26 with the server 22. The templates act as road maps to direct the health care professional in developing the care plan, ensuring that all appropriate questions are addressed. In addition to the template, the health care professional can add features to the care plan based on physician's notes, personality traits of the patient, etc. to further tailor each care plan to an individual patient. To this end, the patient's clinician has a means to see the patient's daily list of media elements to be complete. The clinician also sees when each media item was started, stopped, and status (unopened, in progress, complete, etc.) All of these factors can be used by the health care professional in initially designing the patient's care plan, or modifying the care plan after the commencement of the care plan.

Based on the care plan template, the server 22 compiles a care plan for the patient. The server 22 selects the specific content elements (videos, surveys, still pictures, audio files, requests for patient input, etc.) that will be a part of the patient's care plan. The server 22 also decides in what general order the content should be presented to the patient. It is to be understood, however, that ultimately the care plan designer has the option to order the content differently, based on type of content, topic, and other factors. The care plan designer has the ability to edit media files or the logic branching between files to improve the narrated experience that accompanies the care plan elements on the patient's user interface device 12. The server 22 is in periodic communication with the set top box 12 of a particular patient. On an ongoing basis, the server 22 receives information and feedback about the patient's progression through the prescribed material, and selects new content elements for presentation to the patient as they become appropriate. For example, a diabetic will receive general and overview information about diabetes at first, and as the patient progresses through that material, the server 22 will select more detailed and specific content more directed to the particular patient based both on the care plan template and progress and understanding of the patient.

With reference to FIG. 2, and continuing reference to FIG. 1, the care plan is generated in step 30. When a patient logs onto the system using their interface device 12, an itinerary arrangement processor 32 organizes content for today's viewing by the patient into a serially arranged guided encounter in step 34. The itinerary arrangement processor can either be in the server 22 or in the interface device 12. In the server embodiment, the server 22 generates the guided encounter and transmits it to the interface device 12 in advance of when it is supposed to be viewed, or as it is to be viewed. In one embodiment, the server 22 streams content to the user interface device 12 as it is being viewed, or accesses and releases content that is stored on the user interface device 12. In another embodiment, the itinerary arrangement processor 32 is housed in the user interface device 12. In this embodiment, the server 22 transmits the identity of the content that the patient should view, and then the itinerary arrangement processor 32 arranges the content into a guided encounter. When the data is stored locally on the user interface device 12, the itinerary arrangement processor 32 takes content that is selected for today's viewing and arranges it into a simple, easy to understand presentation of a guided encounter to be viewed on command by the patient.

Once the content elements have been arranged into a guided encounter for the patient, the interface device 12 is prepared to present the guided encounter to the user. When the patient powers up the user interface device 12, they come to a welcome screen such as the one depicted in FIG. 3. In step 36, the patient logs on to the network by entering a patient identification code. The patient enters the code by pressing the appropriate numbers or letters on the input device 16. FIG. 4 shows an exemplary login screen. This code is to prevent persons other than the patient from accessing the patient's information and programming. Some embodiments can skip the login as a remembered password for those interface devices that have been authenticated. In other instances, the login is required as there may be more than one patient using a given interface device. In one embodiment, the user interface device 12 has previously been established as authentic to the server 22 and is communicating over a secure layer. The patient identification code is for user end security.

After the patient has entered their code correctly, the user interface device 12 displays a patient personalized welcome screen as shown in FIG. 5 to the patient on the display 14. After several seconds, this screen is transitioned to the patient's itinerary for the day, as shown in FIG. 6. (step 38) The entire itinerary for the day is presented so that the patient knows roughly how much material will be covered. In one embodiment, the itinerary will be summarized orally and visually by a nurse narrator. The care plan designer will also be given the tools to link content elements together, such that any narration will relate to the content elements being summarized in text. In some cases the itinerary will provide approximate time durations of the material to be presented such that a patient or user can schedule or plan his/her day. The user interface 12 then prompts the user to indicate when they are ready to begin in step 40. The patient selects "go" or a proceed option in step 42 whenever they are ready, by activating any button on the remote 16 to commence the showing of the first of today's content elements to the patient. The only option for the patient at this point will be to proceed or pause. This way, viewing of the content is automatic. The patient is not able to get lost in sub menus, inadvertently missing content, etc.

Once the patient begins the guided encounter, an overview of the first content element is given as shown in FIG. 7. For example, the user interface device 12 might inform the patient that they are about to watch a video about hypoglycemia, which will last six minutes. The user interface device gives a brief synopsis of the impending content element. Either in response to the user pressing any key or after a set amount of time, the user interface device 12 automatically commences the first content element in step 44, as shown in FIG. 8. Optionally, while a content element is playing, the patient has the ability to pause the content element, and un-pause the content element after pausing. It is to be understood that more options could be given to the patient, but it is desirable to keep the guided encounter simple. After the content element is finished, the patient can be given the option to save the content element for later review in step 46 from a save screen such as the one shown in FIG. 9. Continuing the example, if the patient just watched the video about hypoglycemia, the patient will be given the option to save the video for later viewing. If the patient chooses to save the video, then the patient will be able to access it later through a graphical interface, after today's guided encounter is complete. After the patient selects whether to save the content or not, they are returned to the itinerary screen (FIG. 10) in step 48. Returning to the itinerary screen lets the patient know of their relative progress through the material, e.g., whether they are almost done, or whether they have quite a ways to go. In the example of FIG. 10, the patient can see that watching the video is complete and that there are two elements left to complete.

The user interface device 12 checks to see if there are additional content elements left for display in the guided encounter (step 50). If there are, then the user interface device returns to step 40 and prompts the user to indicate when they are ready to start the next content element, such as by pressing any key. Returning to step 44, one typical content element that can be provided to the patient is a survey or questionnaire. Continuing with the example started above, next, the patient is asked to take a survey, such as the one depicted in FIG. 11, after watching the hypoglycemia video. After the patient provides answers to the survey using the remote 16, the user interface device 12 can check to see if the patient provided satisfactory results to the survey, in step 52. If the patient's answers reflect an adequate understanding of the material, then the patient is returned to the itinerary screen so the user interface device 12 can check to see if there is any additional content left in the itinerary. If the results of the survey are unsatisfactory, the user interface device can review the pertinent information in step 54. Continuing the example of a survey after a video, this may include re-watching the video. Alternately, a series of review screens might be presented to the patient, touching on the most important points of the video, or other satisfactory review. As another option, a more simplified version of the video can be played.

If there are no content elements left, then the user interface device 12 displays an end dialog screen in step 56 that congratulates the patient on a successful completion of today's guided encounter. FIG. 12 shows an example of a congratulatory screen. The patient presses any key to go to a general navigational menu, such as shown in FIG. 13, in step 58. Here, the patient can choose other activities and functions of the system other than those required in today's itinerary. For example, the patient can review previously played saved content, play interactive games, read literature, check their charts, select additional goals, contact a healthcare professional, report unusual symptoms, etc. When the patient is done, they log off of the network 10 in step 60 until a later time.

As an additional content element, the user can provide the system with feedback on their own personal goals concerning what they would like to accomplish, as depicted in FIG. 14. With this information, the itinerary construction processor 32 can select content for future guided encounters that cover material that is more interesting to the patient. By doing this, the patient undergoes more of an interactive experience, tailored to themselves, not generic to all patients with similar health problems.

In the end, it is preferred that the patient can navigate from start to finish of the guided encounter only needing a single button, or possibly few buttons for surveys or queries, on the remote 16. This ensures simplicity for the patient, and helps make sure that the patient does not miss any content elements along the way. Barring any unusual happenings, the guided encounter is preferably performed in the above-described manner. The patient might voluntarily terminate the session early, such as after failing the quiz, or may terminate for reasons out of the patient's control. For instance, perhaps the patient's power goes out, or the patient's dog chews on the power cord, or the patient prematurely powers off the user interface device 12. In one exemplary embodiment, the system records the experiences a patient has completed and not completed in a viewing session encounter. If the patient does not complete a session, the next time the patient logs in, a reminder is given of the completed material and material that is still to be completed. Portions of the encounter that are time sensitive in nature, or would be burdensome if they build up can be delete by the system. The timing of the care plan deliveries can be adjusted such that delivery of the uncompleted element(s) is rescheduled for delay sequentially in upcoming sessions. In another embodiment, the next time the patient logs on to the network 10, the guided encounter will be started from the beginning. In another embodiment, the encounter will start from the beginning of the content element that was interrupted or at the beginning of the next element if the interrupted element was substantially completed. In yet another embodiment, the patient will be given the option of selecting a starting point anywhere in the guided encounter where the content elements have already been started. It is also contemplated that there may be points within the content elements that prompt the patient to press a button on the remote 16 in order to continue, to ensure that the patient is still being attentive. Other situations that may arise and interrupt the guided encounter are possible, and similarly, ways to restore the encounter as seamlessly as possible are also desired. In the end, the patient should receive a linear presentation of several content elements with no more effort than using a single button on the remote 16. In another embodiment, the remote may be as simple as an enter button and up and down keys to step to different quiz answers.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

Having thus described the preferred embodiments, the invention is now claimed to be:

1. A system for presenting health care information to a patient, the system comprising:
   a computer system that comprises one or more physical processors programmed with computer program instructions which, when executed cause the computer system to:
   extract, from a care plan including a series of content elements to be presented over time to a patient, content elements to be displayed to the patient in a viewing session;
   generate a serially ordered itinerary for presentation to the patient using the extracted content elements, and at least partially tailor the selection of content elements to at least one personal patient goal associated with the patient;
   display, using a display device connected to an user interface device, one of the content elements to the patient;
   receive, using an user input device, a predetermined level of feedback from the patient to continue display of next content elements;
   repeat the steps of displaying and receiving until all the extracted content elements have been displayed to the patient or the viewing session terminates; and
   reschedule any uncompleted elements of the viewing session for upcoming viewing sessions, when the viewing session terminates prior to completion.

2. The system of claim 1, wherein the user input device includes at least one key, which is activated by the patient to display one of the content elements, and actuated again to display the next content element.

3. The system of claim 2, wherein the user input device includes a plurality of keys, activating any of the keys cause the next content elements to be displayed.

4. The system of claim 1, wherein the one or more physical processors are located in the at least one user interface device.

5. The system of claim 1, wherein the display device is a television set in the patient's home.

6. The system of claim 1, further including:
   a look-up-table that houses completed care plan templates for each patient for access by the computer system.

7. The system of claim 1, further including:
   a health care professional interface to the computer system that allows a health care professional to create and modify patient care plans.

8. The system of claim 7, wherein the health care professional interface includes a content management system that aids the health care professional in creating and modifying care plans by allowing the health care professional to upload, version, and preview content before it is distributed to patients.

9. A method of presenting health care information to a patient, the method being implemented in a computer system that includes one or more physical processors configured to execute one or more computer program modules, the method comprising:
   extracting, from a care plan including a series of content elements to be presented over time to a patient, content elements to be displayed to the patient in a viewing session;
   generating a serially ordered itinerary for presentation to the patient using the extracted content elements, and at least partially tailor the selection of content elements to at least one personal patient goal associated with the patient;

displaying, using a display device connected to an user interface device, one of the content elements to the patient;

receiving, using an user input device, a predetermined level of feedback from the patient to continue display of next content elements;

repeating the steps of displaying and receiving until all the extracted content elements have been displayed to the patient or the viewing session terminates; and rescheduling any uncompleted elements of the viewing session for upcoming viewing sessions, when the viewing session terminates prior to completion.

10. The method as set forth in claim 9, further including:

after displaying all content elements in the viewing session's itinerary to the patient, displaying an end content element indicating the completion of the viewing session's itinerary to the patient, and after displaying the end content element, allowing the patient to select the same or other content elements for review in a patient selected order.

11. The method as set forth in claim 9, wherein the steps of extracting and generating are performed by the one or more processors at one of the patient's home or remote from the patient's location.

12. The method as set forth in claim 9, wherein the viewing session's itinerary is downloaded to the user interface device prior to a scheduled user login.

13. The method as set forth in claim 9, wherein the receiving includes activating a single key on the user input device to cause the next content element to be displayed.

14. The method as set forth in claim 9, further comprising after the patient logs on to a secure health care information network, prompting the patient to commence the viewing session's itinerary;

after the patient selects a commencement action, displaying the one of the content elements to the patient.

15. The method as set forth in claim 13, wherein the user input device includes a plurality of keys and pressing any key causes the first or next content element to be displayed.

16. The method as set forth in claim 9, wherein after displaying the viewing session's itinerary, pressing any key of the user input device causes the first or next content element to be displayed.

17. The method as set forth in claim 16, wherein the receiving includes pressing any key of the user input device to cause the next content element to be displayed, such that the order of displaying the content elements is constrained.

18. The method as set forth in claim 9, wherein at least one of the content elements is a survey, and further including:

prompting the patient to supply answers to the survey;
checking the patient's answers for accuracy; and,
if the patient supplies unsatisfactory answers to the survey, displaying content elements appropriate for improving the patient's comprehension of material related to the survey.

19. The method as set forth in claim 9, further including:
uploading content for inclusion in the care plan, and previewing the content to a health care professional before it is presented to the patient.

20. A non-transitory electronic storage media comprising computer program instructions that, when executed by one or more physical processors, perform a method for presenting health care information to a patient, the computer program instructions comprising:

instructions for extracting, from a care plan including a series of content elements to be presented over time to a patient, content elements to be displayed to the patient in a viewing session;

instructions for generating a serially ordered itinerary for presentation to the patient using the extracted content elements, and at least partially tailor the selection of content elements to at least one personal patient goal associated with the patient;

instructions for displaying, using a display device connected to an user interface device, one of the content elements to the patient;

instructions for receiving, using an user input device, a predetermined level of feedback from the patient to continue display of next content elements;

instructions for repeating the steps of displaying and receiving until all the extracted content elements have been displayed to the patient or the viewing session terminates; and instructions for rescheduling any uncompleted elements of the viewing session for upcoming viewing sessions, when the viewing session terminates prior to completion.

21. The non-transitory electronic storage media of claim 20, further including:

instructions for allowing, using another user interface, a nurse or other health car professional to at least one of enter, amend, and preview care plans or content elements.

22. The system of claim 1, wherein the predetermined level of feedback is based on the level of experience the patient has with operating electronic devices.

23. The system of claim 1, wherein the predetermined level of feedback is based on characteristics of a treatment of the patient.

* * * * *